United States Patent [19]

Pfefferkorn

[11] 4,302,329

[45] Nov. 24, 1981

[54] INSTALLATION FOR THE RECOVERY OF METHANE GAS FROM ORGANIC WASTE

[76] Inventor: Herbert Pfefferkorn, Arlbergstrasse 101, 69 Bregenz, Vorarlberg, Austria

[21] Appl. No.: 107,610

[22] Filed: Dec. 27, 1979

[30] Foreign Application Priority Data

Jan. 3, 1979 [AT] Austria .................................. 51/79
Jul. 25, 1979 [AT] Austria ................................ 5146/79

[51] Int. Cl.³ .................................................. C02F 3/28
[52] U.S. Cl. .................................... 210/97; 210/138; 210/180; 210/195.3; 210/258
[58] Field of Search ..................... 210/2, 3, 4, 12, 16, 210/180, 195.1, 194, 258, 603, 605, 613, 741, 744, 195.3, 97, 120, 138; 422/230; 435/3, 167, 289, 287, 801, 813; 137/132, 136, 142

[56] References Cited

U.S. PATENT DOCUMENTS

| 1,314,955 | 9/1919 | Flicker | 435/167 |
|---|---|---|---|
| 1,420,250 | 6/1922 | Gavett | 210/2 |
| 1,690,682 | 11/1928 | Imhoff | 435/167 |
| 1,918,678 | 7/1933 | Wirz | 137/132 |
| 2,889,929 | 6/1959 | Kivell | 210/194 |
| 2,892,545 | 6/1959 | Griffith | 210/16 |
| 3,010,581 | 11/1961 | Knapp | 210/16 |
| 3,494,462 | 2/1970 | Baud | 137/142 |
| 3,596,672 | 8/1971 | McBee | 137/142 |
| 3,631,885 | 1/1972 | Hanson-Graville | 137/142 |
| 3,768,652 | 10/1973 | Jardim | 210/258 |
| 3,782,453 | 1/1974 | Cates | 137/142 |
| 3,981,803 | 9/1976 | Coulthard | 435/167 |
| 4,165,285 | 8/1979 | Wind | 210/195.3 |

FOREIGN PATENT DOCUMENTS

2409305  7/1979  France ................................. 435/167

Primary Examiner—Ernest G. Therkorn
Attorney, Agent, or Firm—Toren, McGeady & Stanger

[57] ABSTRACT

The invention relates to an installation for the recovery of methane gas from organic waste with a fermentation space, a gas collecting space and a post-fermentation space, as well as with at least one supply line into the fermentation space and one offtake for the excess, fermented liquid from the post-fermentation space, the spaces being heat-insulated and preferably embedded at least partially in the ground, and the post-fermentation space, which preferably is arranged above the fermentation space, being connected in the manner of communicating vessels with the fermentation space, preferably in one structural unit.

24 Claims, 12 Drawing Figures

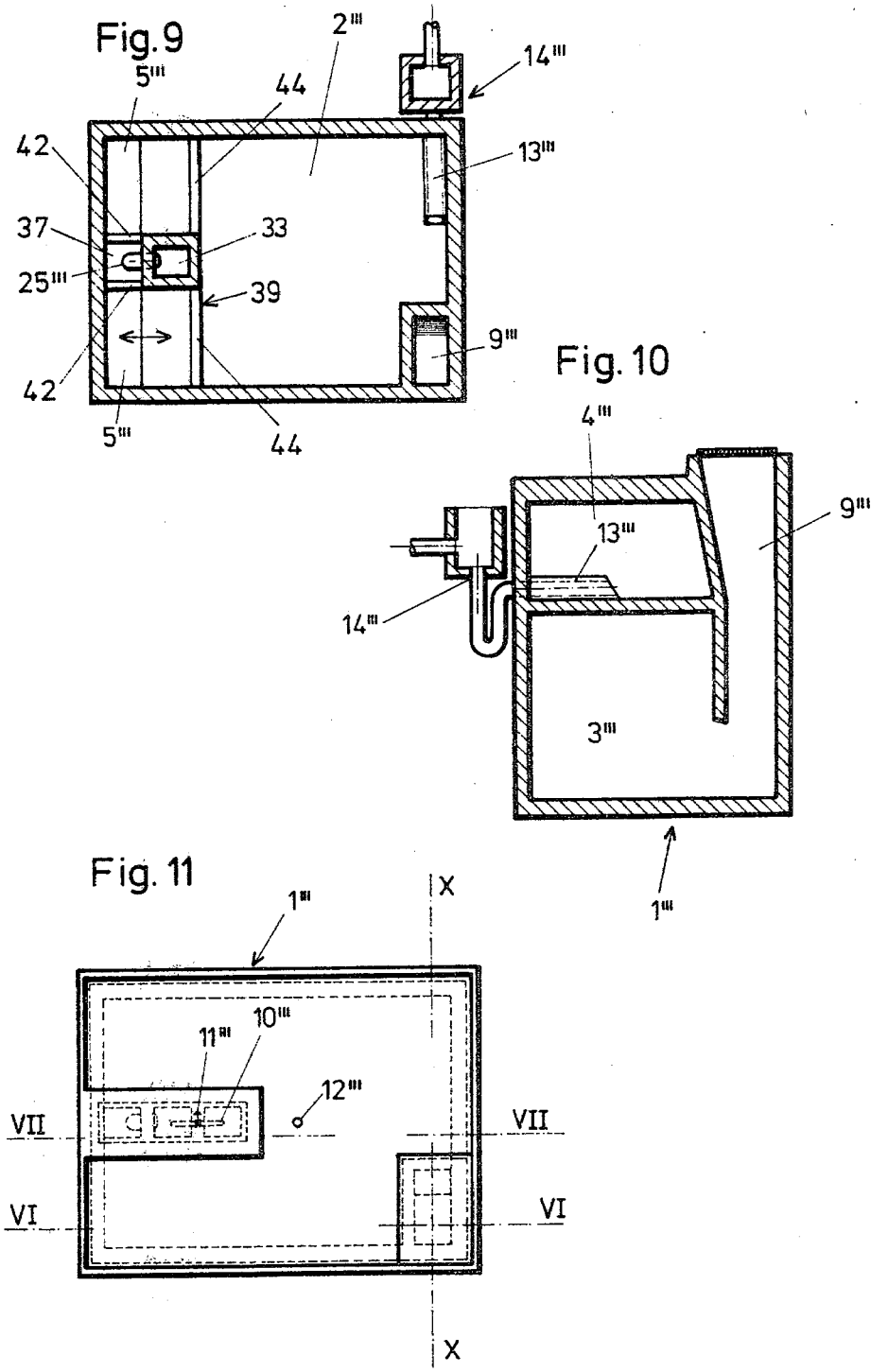

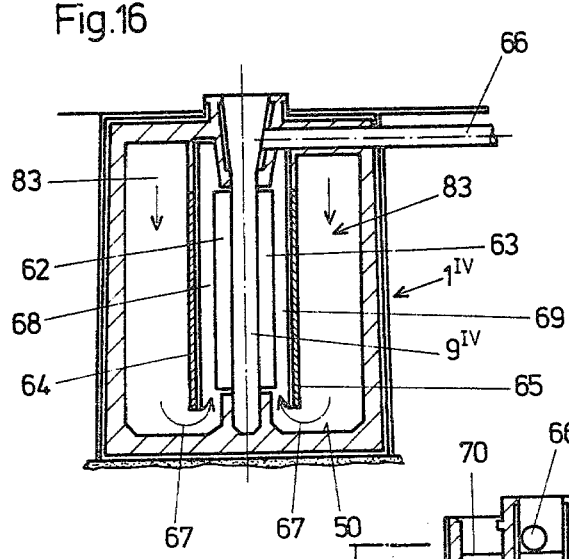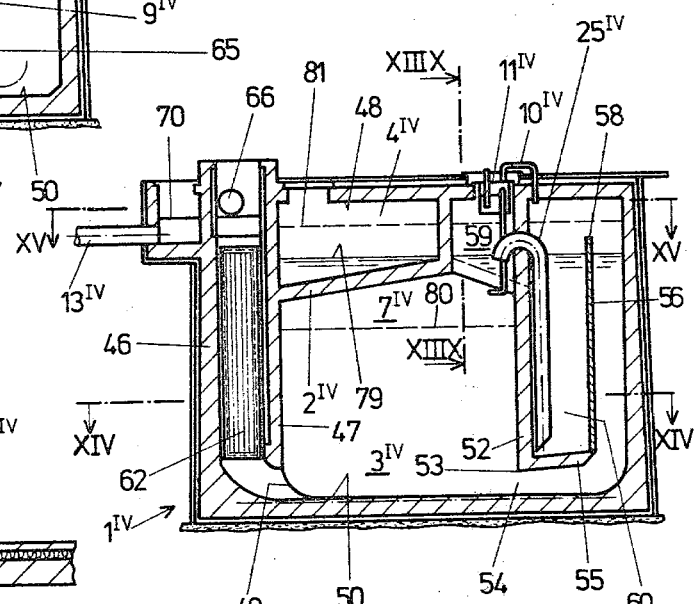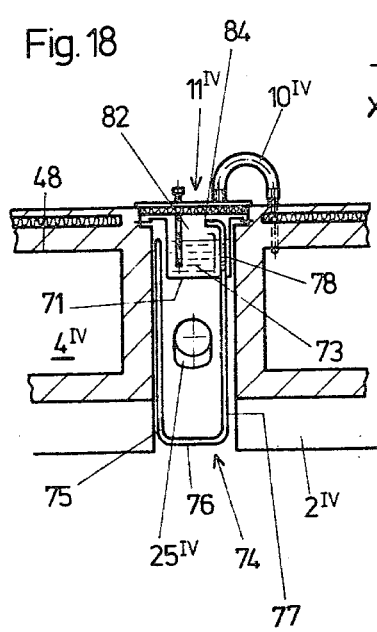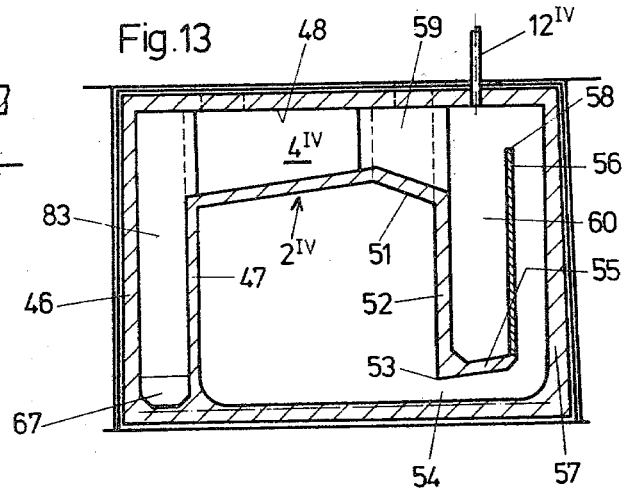

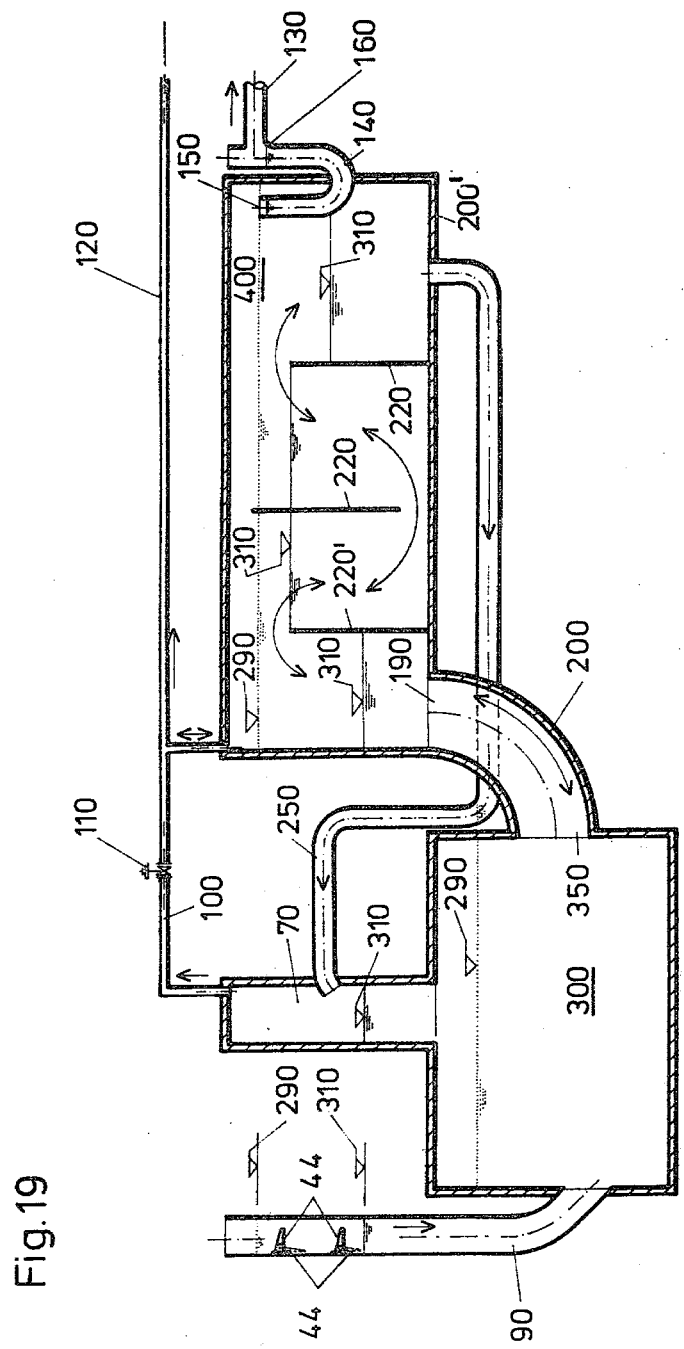

INSTALLATION FOR THE RECOVERY OF METHANE GAS FROM ORGANIC WASTE

Publications, which have been taken into consideration for delineating the state of the art: "Recovery and Utilization of Methane from Sewage Sludge and Dung", Volume III, Published by Oldenberg in 1956, Pages 244–246.

Installations for methane recovery are a part of the state of the art. When constructing installations for the recovery of methane gas, microbiological factors must be taken into account in order to achieve the highest possible gas yield. At the same time, it is important to ensure that only so much fresh sludge is supplied to the installation, that the volatile acids content remains below a certain percentage, that the medium is reacting under alkaline conditions, that the temperature remains uniform and that there are no sudden temperature jolts, and, finally, that the escape of the gas is not hindered by the formation of a floating layer. In other words, an advantageous production of methane is primarily a technical problem of charging and organizing the fermentation spaces, as well as especially of eliminating the floating layer. A plant has become known, in which, by the intermittent throttling of the gas being removed and the constant evolution of gas, a pressure is produced which is utilized for loosening the floating layer. At the same time, the fermentation container is charged with filling material through two external shafts. The structural unit comprises a fermentation space, a gas container and a sludge silo. The fermentation container is the lower part of the structural unit, whose upper part functions as a gas container. The sludge container is located above the gas container. It is in the shape of a flat funnel, which is connected at its lowest point by a vertical channel with the lower part of the fermentation container and which has an outlet at the side for excess fermenting liquid. A grid is mounted in the other part of the fermentation container or in the lower part of the gas container. These two parts are not separate, but form a structural unit. The filling material is introduced through the filler shaft and so reaches the lower part of the fermentation container. The gas, which is liberated in the fermentation container, rises upwards and is collected in the gas collecting space. With increasing formation of gas, a pressure is developed which forces the liquid from the fermentation container through the vertical shaft into the sludge container which is located above the gas space. As soon as the gas is removed, the pressure in the gas container is reduced and the liquid drops from the sludge container above through the vertical shaft downwards back into the fermentation space. If no gas is removed, the pressure increases as a result of the constant evolution of gas, and raises the liquid from the fermentation container back into the sludge container. Consequently, the level of the liquid in the fermentation container is constantly in the process of rising and falling, as is naturally also the floating layer, which is lying on the liquid level. In so doing, the floating layer is supposed to be broken up by the grip between the fermentation space and the gas space to such an extent, that it permits the gas to escape from the gas space. By the intermittent throttling of the gas removal and the constant evolution of gas, a pressure is produced here, which is utilized for breaking up the floating layer and for removing the degassed materials from the fermenting system. This equipment must not however have been a success, because only a single example of this construction has been erected. The reason for this may well lie in the fact that no satisfactory engineering solution has yet been offered for the required, intermittent throttling of the removal of the gas so that the formation of the floating layer cannot be prevented reliably. The emergence and development of this floating layer however paralyse the installation within a short time and make it unfit for practical use.

The invention now represents a direct further development and improvement of this known installation, with the objective of being able to use installations of this type economically and on a large scale. This can be achieved inventively be connecting the upper part of the post-fermentation space on the one hand, through a connecting pipe blocked by a valve, with the gas-collecting space and, on the other, with at least one gas-removal pipe which leads to a pressure equalizing container, the offtake being connected through a hydraulic siphon-like closure with the post-fermentation space. Thanks to this proposal, the rise and fall of the floating layer, which is necessary for its effective destruction, no longer is dependent on the more or less arbitrary removal of gas; rather, the floating layer rises and falls in a rhythm, which can be made exclusively dependent on the extent of the evolution of gas or which is dependent on this evolution. If the installation is charged at a steady rate, a steady evolution of gases over a unit period of time can be expected. It is therefore moreover expedient if the valve opens and closes the connecting pipe as a function of time and/or as a function of the height to which the gas space is filled and/or as a function of the gas pressure in the gas-collecting space. Because the structural unit for the recovery of methane gas is to be erected primarily in agriculturally used areas, it is important that this structural unit has a relatively simple design. For this reason, it is proposed, according to a further characteristic of the invention, that the post-fermentation space be mounted at the side of the gas-collecting space and that the post-fermenting space and the gas-collecting space have layers at equal levels and that the connecting opening to the fermenting space and the opening for the offtake are arranged at opposite ends of the post-fermenting space.

A further characteristic of the invention, whose function it is to destroy the floating layer and through which it is achieved that the floating layer is wetted regularly from above, lies therein that the gas-collecting space is connected with the post-fermentation space through a siphon and that the inlet opening of the syphon is arranged in the bottom area of the post-fermentation space and the outlet opening in the upper area of the gas-collecting space.

Examples of the operation are described in greater detail and the advantages, which result therefrom, are explained by means of the drawing.

Figure 5:
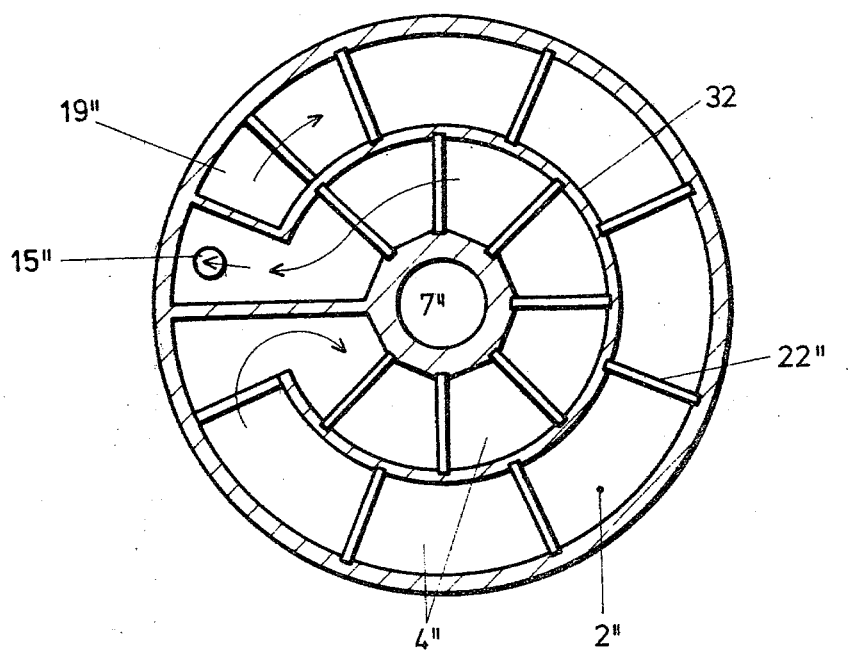
Figure 2:
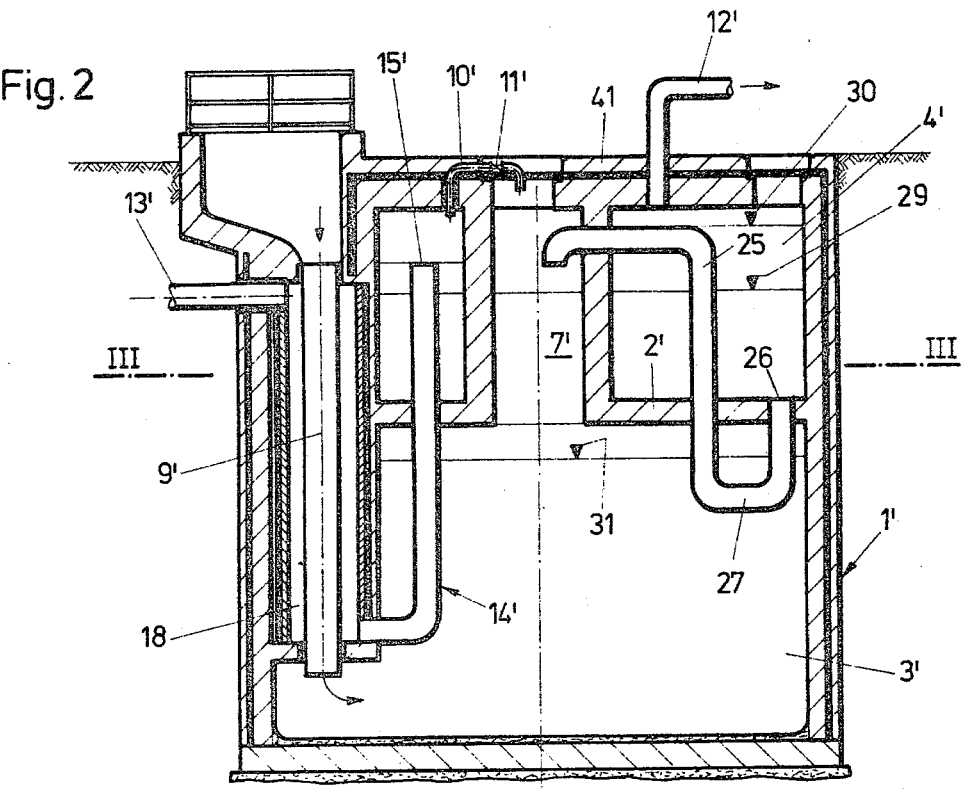
FIG. 2 shows a vertical section through a cylindrical plant.
Figure 4:
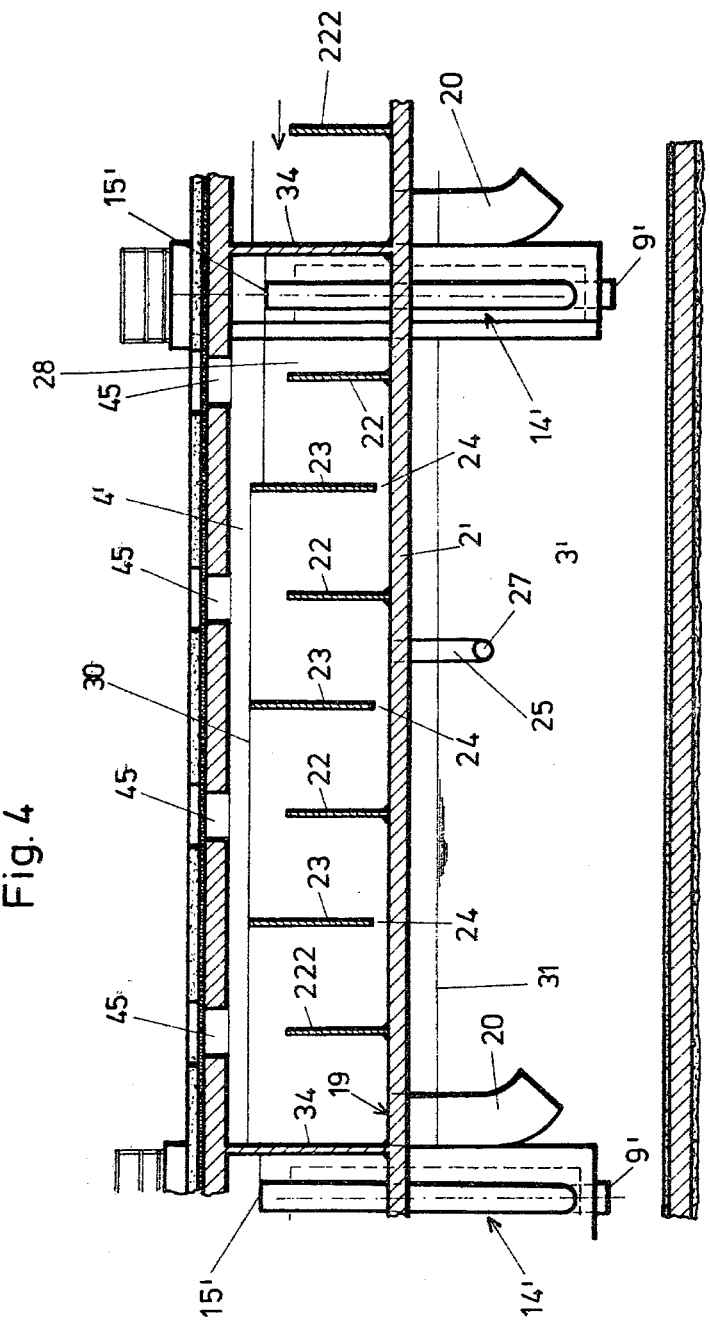
Figure 6:
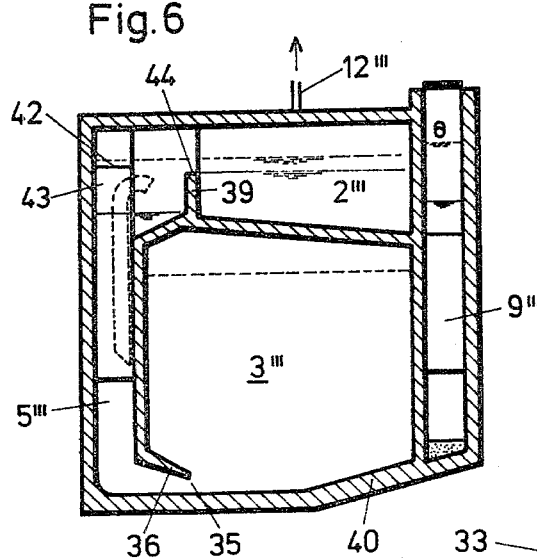
Figure 7:
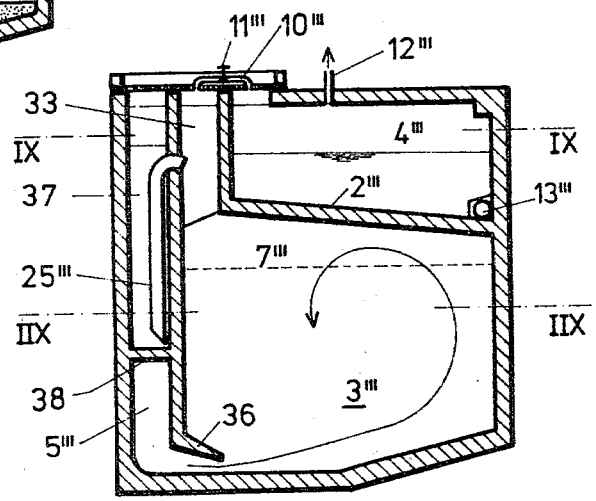
Figure 8:
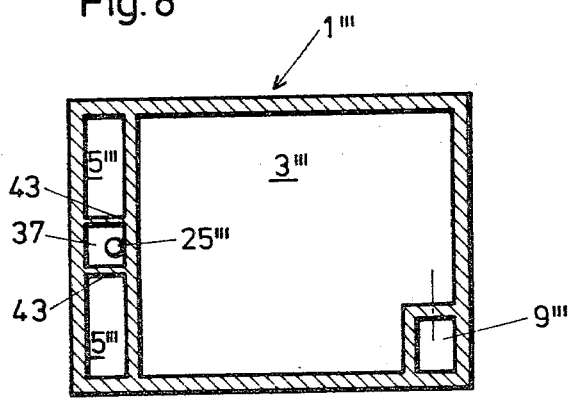

FIG. 4 an internal arrangement of the structure shown in FIG. 2;

FIG. 5 shows a different arrangement of an upper ring-shaped space according to FIG. 2 in horizontal cross section;

FIGS. 6–11 show a further plant and moreover FIG. 6 illustrates a first vertical section along the line VI—VI in FIG. 11;

FIG. 7 shows a second vertical section along the line VII—VII in FIG. 11;

FIG. 8 shows a horizontal section along the line IIX—IIX in FIG. 7;

FIG. 9 shows a horizontal section along the line IX—IX in FIG. 7;

FIG. 10 shows a vertical section along the line X—X in FIG. 11 and

Figure 17:
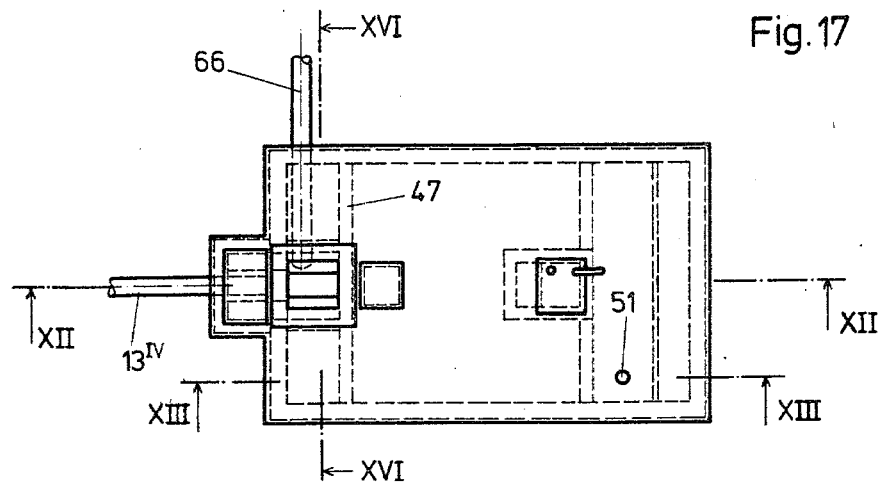
Figure 14:
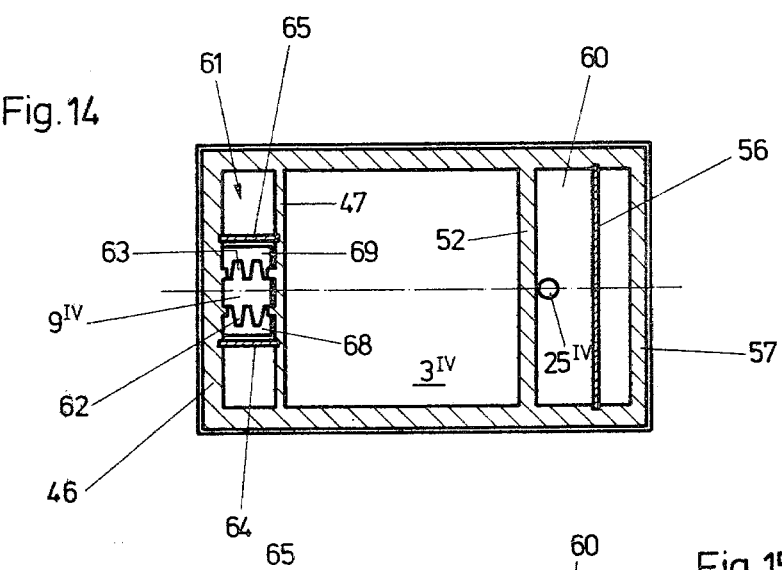
Figure 15:
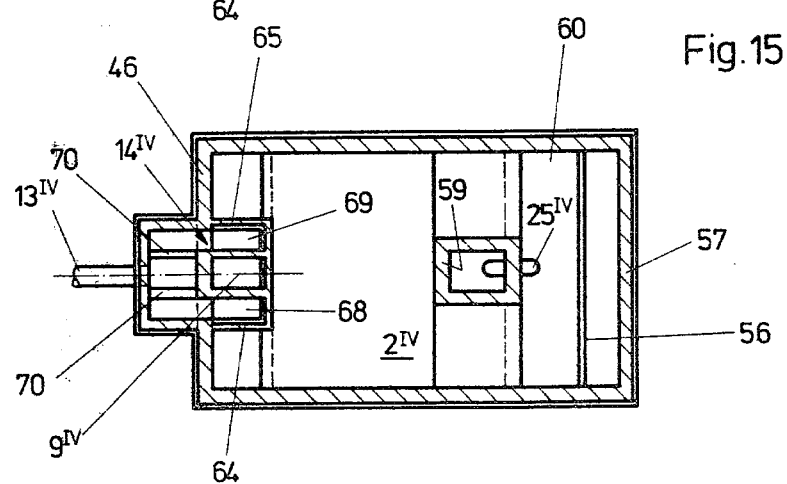

FIG. 11 shows a plan view;

FIGS. 12–18 illustrate a further example of the operation;

FIG. 12 shows a central longitudinal section through the installation along the profile line XII—XII in FIG. 17;

FIG. 13 shows a second longitudinal section along the profile line XIII—XIII in FIG. 17;

FIG. 14 shows a horizontal section along the line XIV—XIV in FIG. 12;

FIG. 15 shows a second horizontal section along the line XV—XV in FIG. 12;

FIG. 16 shows a cross section along the line XVI—XVI in FIG. 17 and;

FIG. 17 shows a plan view of the installation;

FIG. 18 shows a detail from FIG. 12 on an enlarged scale along the profile line XVIII—XVIII (automatic valve);

FIG. 19 shows the principal construction of the structural solutions shown in FIGS. 2 to 18, the fermentation space and the post-fermentation space being shown as separate structures in this figure for the purpose of illustration.

Figure 1:
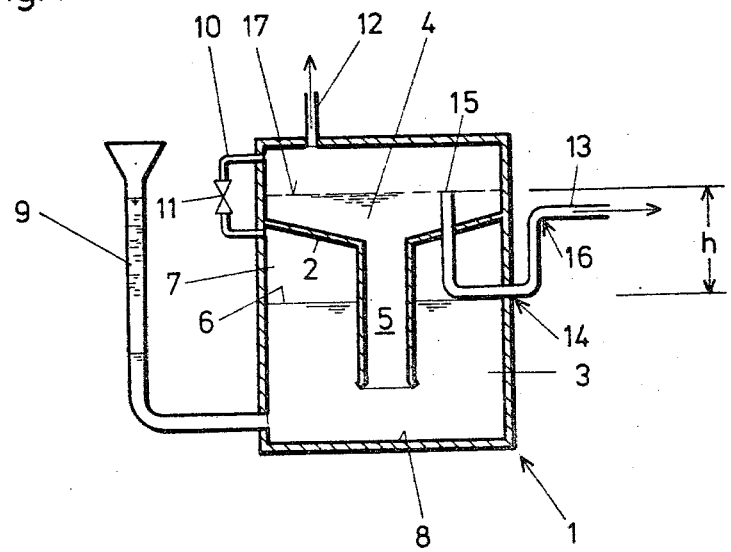
FIG. 1 shows a vertical section through the principal structure of a facility for recovering methane gas.

FIG. 1 represents a vertical section of the principal structure of an installation for the recovery of methane gas. A cylindrical structure 1 with a vertical axis, which is heat-insulated and moreover has wall sections which are at least partially heated, is set completely or at least partially in the ground, depending on the local conditions where this structure is erected or set up. Through an internal false ceiling 2, the structure is divided into two spaces, namely the fermentation space 3 and the gas-collection space 7 on the one hand and the post-fermentation space 4 on the other. The fermentation space 3 and the gas-collection space 7 are not separated structurally from each other. A vertical shaft 5, arranged centrally here, connects the two spaces 3 and 4 in the manner of communicating vessels. The concept of communicating vessels is to be understood here and in the following in the sense that the liquid in these two spaces has, at least partially, the possibility of flowing back and forth. Here and in the following, the fermentation space 3 is understood to be that space which is filled with the liquid from which the gas is to be drained. Directly above the fermentation space 3 is the gas-collection space. These spaces change their volume during the operation of the installation and it is pointed out once again here that these two spaces are not separated structurally from each other. The filling shaft 9, which is located at the side and through which the waste is introduced, discharges near the bottom 8. The gas collection space 7 is connected with the upper portion of the post-fermentation space through a connecting pipe 10. This pipe can be opened up and closed off by a valve 11. A further pipe 12 leads from the upper part of the post-fermentation space 4 to a pressure-equalizing container (which is not shown here), for example a gasometer, so that the installation constantly operates at a steady operating pressure. An offtake 13 discharges the fermented liquid from the post-fermentation space 4, for which purpose a siphon-like hydraulic closure 14 is provided between the post-fermentation space 4 and pipe 13. Valve 11 of the connecting pipe 14 is controlled in a time-dependent manner here. It is however also possible to control this valve 11 as a function of the gas pressure in the gas-collecting space 7 or as a function of the respective height of filling. The inlet opening 15 of the offtake 13 or of the hydraulic closure 14 is located in the upper region of the post-fermentation space 4 and moreover within or above the horizontal plane described by the overflow edge 16 of the hydraulic closure 14.

In principle, the installation operates as follows. It is assumed that liquid is present in the fermentation space 3 and in the post-fermentation space 4, that valve 11 is closed and that a pressure has already developed in the gas-collecting space 7, so that the column of water of height h is able to maintain the equilibrium. The filling shaft 9 is also partially filled because of its communicating connection with the gas space 3. The external air pressure acts on the level in the filling shaft 9 so that the level of the liquid is higher in this filling shaft than in the fermentation space 3. Gas continues to be evolved from the filled material in the fermentation space 3. The amount of gas and, at the same time, the gas pressure continued to increase in the gas collection space 7. This causes a further portion of the liquid, which is still present in the fermentation space 3, to be forced upwards through the connecting shaft 5 into the post-fermentation space 4. As a result, the lower liquid level 6 falls and the upper liquid level 17 rises somewhat, a portion of the liquid, which has been displaced upwards and which is already fermented, flows over the offtake 13 into a collection space which is not shown here. The pressure, developed in the gas-collecting space 7, controls valve 11. If the pressure is sufficiently high, valve 11 is opened and the pressure in the gas-collection space 7 drops suddenly, the rate of drop of the gas pressure depending on the cross section of the connecting pipe 10. Accordingly, the pressure equalizes between the post-fermentation space 4 and the gas-collecting space 7. This sudden drop in pressure in the gas-collection space 7 now causes a portion of the liquid in the upper post-fermentation space 4 to fall downwards through the vertical shaft 5, so that the liquid level 6 in the fermentation space 3 once again rises. This takes place with vigorous turbulence. On the other hand however, the liquid level in the upper post-fermentation space 4 drops. This process takes place periodically, the duration of the individual periods being dependent on the vigor and intensity of the evolution of gas in the fermentation space 3. The formation of a floating layer is largely prevented by this periodic rise and fall in the level of the liquid. The lower spaces 3–7 may of course be additionally equipped with rupture edges which, as the liquid level rises or falls, act on the floating layer, destroying it mechanically.

The process described is repeated as soon as valve 11 is closed and pressure once again begins to build up in the gas-collecting space 7.

Figure 3:
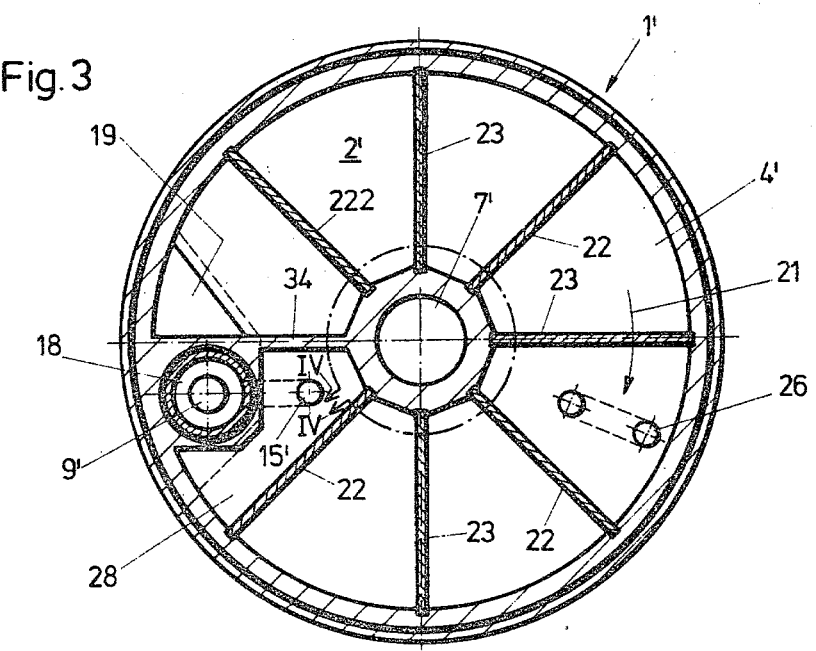
FIG. 3 shows a horizontal section along the line III—III in FIG. 2.

A first, structural variation of the design principle shown in FIG. 1 is now illustrated in FIGS. 2, 3 and 4. In the following examples of the operation, the same parts have been provided with the same reference numbers to which one or more index marks have been added for the purpose of differentiation.

Structure 1', which here is also heat-insulated, provided with heated wall sections and, at least partially, set in the ground, is formed by a vertical cylinder. The post-fermentation space 41' is formed here by a ring-shaped chamber, which surrounds the gas-collecting space 7'. The false ceiling 2' separates here the fermentation space 3' and the post-fermentation space 4'. The ceiling 41 of structure 1' forms the upper boundary of the gas-collecting space 7' as well as the post-fermentation space 40'. The filling shaft 9' is integrated here in the structure 1'. Along a portion of its length, the filling shaft 9' passes through an outwardly heat-insulated length of pipe 18, which in turn represents a U-shaped, siphon-like, hydrolic closure 14', which leads to the outside to the offtake 13'. The false ceiling 2' has an inlet opening 19, from which a section of pipe 20 leads into the fermentation space 3', as can be seen from FIG. 4. In FIG. 2, this section of pipe is hidden by pipes 9' and 18. Looked at in the direction of flow (arrow 21, FIG. 3), vertical wall panels 22–23 are arranged in the ring-shaped post-fermentation space 4' at a distance from one another. In alternating sequence, these wall panels are connected with the bottom 2' or raised from the bottom with the formation of a gap 24. In the example of the operation, which is shown here, a siphon line 25 is also built in, which connects the gas-collection space 7' with the post-fermentation space 4' The inlet opening 26 of this siphon line 25 is located in the false ceiling 2'. From here, the siphon line 25 is passed downwards through a siphon-like elbow 27 and then rises once again so as to discharge into the gas-collecting space 7' (FIG. 2). From a practical point of view, the siphon line is arranged so that its inlet opening 26 is located in chamber 28 of the post-fermentation space 4', which is the last chamber when looking at the Figure in the direction of flow (arrow 21). However, for reasons of clarity, a different arrangement has been chosen for the example of the operation shown (FIGS. 2, 3 and 4). The gas-collection space 7' is connected here with the post-fermentation space 4' through the connection pipe 10'. The time/volume-controlled and/or pressure-controlled valve 11 is mounted in this connecting pipe 10'. Pipe 12' leads from the post-fermentation space to a pressure-equalizing container (gasometer), which is not shown. FIG. 4 represents a section along the line IV—IV in FIG. 3, whereby the Figure, obtained through this section, is developed in the plane of the drawing. Compared to FIGS. 2 and 3, the scale for FIG. 4 is reduced.

Assuming that the equipment has been filled but that gas has not yet been evolved, the level of filling is described by the level marker 29. Methane gas, which is subsequently evolved in the fermentation space 3', rises and collects in the gas-collecting space 7'. The resulting gas pressure presses the liquid in the fermentation space 3' downwards and the liquid, so displaced, rises over the section of pipe 20 up into the post-fermentation space 4' and moreover until the level, given here in FIG. 2 by markers 30 and 31, has been reached. The upper level (marker 30) is above the siphon line 25 and the lower level (marker 31) barely above the elbow 27. In chamber 28 of the post-fermentation space 4', the level is determined by the position of the inlet opening 15'. A portion of the liquid in the post-fermentation space 4' flows to the outside over the offtake 13'. If valve 11' of the connecting pipe 10' is now opened, there is a sudden equalization of pressure between the two spaces 3' and 4'. In so doing, a portion of the liquid in the post-fermentation space 4' flows back through the opening 19 in the bottom and through the pipe section 20 into the post-fermentation space 3' and provides for the appropriate turbulence and mixing of the liquid in the fermentation space 3', while a different portion of liquid is passed from the post-fermentation space 4' through the siphon line 25, which has now become active, into the gas-collecting space 7, from where it falls from above onto the floating layer, which it wets thoroughly and at the same time supplies with strains of bacteria from the post-fermentation space, so that a kind of inoculation process takes place. When the pressure has fully equilibrated, valve 11' once again is closed, the evolution of gas commences once more and the process described is repeated.

The arrangement, which is shown here by means of a structure which is round in cross section, can also be realized in a rectangular structure. It can furthermore been seen from FIGS. 3 and 4 that the wall panels 34 subdivide the ring-shaped post-fermentation space 4', so that this ring-shaped space has a finite boundary. It should furthermore be pointed out that the amount of liquid, which flows back into the fermentation space 3' as the pressure is equalized by opening valve 11, is determined by the height of partition 222, which is immediately adjacent to the inlet opening 19 in the bottom. The post-fermentation space 4' is accessible from above through shafts 45, which are closed off with lids.

In the example of the application shown, the liquid moreover flows through the ring-shaped space, which forms the post-fermentation space 4 (see FIG. 3), over the whole width of the sapce in each case in one direction. FIG. 5 now shows a horizontal section, which corresponds to that of FIG. 3, in which however this ring-shaped space can be subdivided by a dividing wall 32 into two flow zones in which the liquid flows in opposite directions. Wall panels 22" are drawn here whose lower edge is detached from the bottom 2" and whose upper edge is detached from the ceiling of the post-fermentation space 4". In addition, these panels are inclined alternately, so that the intensive flow, which develops as the pressure is equalized by opening the valve, vigorously mixes the liquid. FIG. 5 also represents a design variation of the post-fermentation space of FIG. 3.

FIGS. 6–11 show a further construction, in which structure 1''' essentially is quadratic. In this structure 1''', the fermentation space 3''' and the gas-collecting space 7''', which here still change over into a gas dome 33, form a common volume, which is separated from the post-fermentation space 4''' above by the inclined false ceiling 2'''. Two vertical shafts 5''', provided at the front, connect the fermentation space 3''' with the post-fermentation space 4''' (FIG. 6). The lower discharge opening 35 is located in the bottom region of the fermentation space 3''' and leads over an outer, slanting apron 36 to the actual vertical shaft 5'''. Between the two vertical shafts 5''', a sack-like shaft 37 is provided (FIG. 7), which forms a portion of the post-fermentation space 4''' and whose bottom 38 is located below the false ceiling 2'''. The top edges 42 of the side walls 43, which form the boundary of this sack-like shaft 37, can be seen in FIGS. 6 and 9. In this sack-like shaft 37, there is a siphon line 25''', whose discharge opening is close to the bottom 38 of this shaft 37 and whose other opening projects into the gas dome. (FIG. 7). In the region at the top of the slanting false ceiling 2''', a sideboard 39 is provided, whose top edge 44 is above the upper knee of the siphon line 35, yet below the top edge 42 of the walls 43. The filling shaft 9''' is integrated here in the structure 1''' and arranged in one corner of the same. The connecting pipe 10''', with the pressure-equalizing valve 11''' connects here the upper region of the dome 33 with the upper region of the post-fermentation space 4''' (FIG. 7). The offtake 13''' here also leads over a hydraulic, siphon-like closure 14''' to the outside. The part 40 of the bottom of the fermentation space 3''', which lies opposite to the outlet opening 35 of the vertical shaft 5''', is somewhat inclined.

The method by which the equipment shown here functions, essentially is evident from what has already been stated and will be explained or supplemented here only briefly for the sake of completeness. It is first of all assumed that valve 11''' is closed, that the same pressure exists in the fermentation space 3''' and in the post-fermentation space 4''' and that the post-fermentation space 4''' and the fermentation space 3''' are filled, the level of filling of the post-fermentation space 4''' being determined by the top edge 44 of the sideboard 39. If now the material, filling the fermentation space 3''' commences to evolve gas, this gas is collected in the dome 33 and subsequently in the gas-collecting space 7''' and the resulting pressure forces the gas-evolving material downwards, the level in the fermentation space 3''' falls and, at the same time, forces a portion of the liquid material through the two parallel, vertical shafts 5''' into the above-lying fermentation space 4''' or, after reaching a certain level (top edge 42), into the shaft 37 with the siphon line 25''', the latter process taking place when the upper level of the liquid has crossed over the difference between the top edges 42 and 44. At the same time, a portion of the excess, already decomposed liquid is also discharged to the outside over the offtake 13'''. When the filling level of the fermentation space 3''' has fallen to the designated extent and the gas pressure in the gas collection space 7''' or in the dome 33 has reached the designated level, valve 11''' is opened, whereby space 33, which is under high pressure, is connected with the post-fermentation space 4''' and, with appropriate dimensioning of the connecting pipe 10''', the pressure in the fermentation space drops suddenly. A portion of the fermenting material now shoots out of the first-fermentation space 4''' or out of the vertical shafts 5''' back into the fermentation space 3''' whereby, as a result of the shape of the bottom part 40 and in conjunction with the apron 36, the liquid material lying here is mixed intensively. At the same time, as a result of the falling liquid level and the falling pressure in dome 33, the siphon line 25''' is activated, so that this siphon line now responds and returns the liquid from shaft 37 into the gas-collecting space. In so doing, this liquid flows from above onto the floating layer in the fermentation space 3''' and thoroughly moistens or wets this from above. Moreover, because a portion of the bacteria are returned from the shaft 37 into the fermentation space 3''', this siphon line 25''' at the same time has a so-called inoculation function. As a result of the alternating rise and fall of the floating layer in conjunction with the thorough drenching of this layer from above through the siphon line, as well as because of the repeated impact of the floating layer against the slanting false ceiling 2''', the floating layer is loosened and broken up or dissolves or even prevented from forming altogether. After the pressure has been equalized and after valve 11''' has once again been closed, the pressure in the fermentation space 3''' again rises and the process described begins once more. Because the gas offtake 12''' is connected with a pressure-equalizing container (gasometer) also here, the equipment works against a constant operating pressure, which is determined by the gasometer. FIGS. 12 to 18 illustrate a further structural variation. This design consists of a structure 1'$^v$ of essentially a rectangular external shape, with a fermentation space 3'$^v$, a gas collection space 7'$^v$ and a post-fermentation space 4'$^v$. Adjacent to the front wall 46, there is a partition 47 which, in its central region, is raised up to the upper, level ceiling 48 of the structure 1'$^v$ and, in its lower central region, however leaves an inlet opening 49; on either side of this central region however it is separate from the ceiling 48 and extends here down to the bottom 50 of the structure 1'$^v$. At about two-thirds the height of this partition, a slanting false ceiling 2'$^v$ is provided, which extends over the whole of the internal width of the structure and which, in the central region of structure 1'$^v$, changes into a gabled roof-like inclined section 51, which rests with its edge on wall 52, whose lower edge 53 is detached from the bottom 50 of the structure in order to form a slit-shaped opening 54 which extends over the width of structure 1'$^v$. The partitions 47 and 52, as well as the gabled roof-like false ceiling 2'$^v$, form the boundary for the fermentation space 3'$^v$. An essentially horizontal apron 55, which is directed away from the fermentation space 3'$^v$, is provided at the lower edge 53 of wall 52. A vertical partition 56, which is detached from the second front wall 57 of the structure 1'$^v$, is connected with the outer edge of the horizontal apron 55. The upper edge 58 of the partition 56 lies below the horizontal ceiling 48 of the structure, but somewhat higher than the ridge edge of the false ceiling 2'$^v$. The roof section 51 carries a dome 59, which forms a portion of the gas-collecting space 7'$^v$ and into which a siphon line 25'$^v$ discharges and in which an automatically operating valve mechanism 11'$^v$ is mounted, which will be explained in detail below. Over the greater portion of its length, the siphon line 25'$^v$ is located in chamber 60 and the discharge opening is taken close to the horizontal apron 55. Chamber 60 is bounded by apron 55 and partition 56.

With the already mentioned partition 47, the first front wall 46 of structure 1'$^v$ forms the boundary of a chamber 61, which is further subdivided by internal bulkhead partitions 62 and 63 and external bulkhead partitions 64 and 65. The internal bulkhead partitions 62 and 63 preferably are constructed of a heat-conducting, chemically stable material, for example, of stainless steel. They are profiled, extend to the bottom 50 of structure 1'$^v$ and form the filling shaft 9'$^v$, into which the feed pipe 66 for the fresh sludge discharges. The external bulkhead walls 64 and 65 extend from the ceiling 48 downwards and, with their lower edges, which are detached from the bottom 50, form the boundary of the flow openings 67, which lead to the vertical shafts 68 and 69 which, together with the overflow edges 70 and the offtake 13'$^v$, form a hydraulic closure 14'$^v$. The overflow edges 70 advisably are mounted so that their height can be adjusted.

As part of the valve mechanism 1'$^v$, a vessel 71 is provided in the dome 59, which is sealed from the dome 59 and the fermentation space 3'$^v$ and whose internal space is connected with the post-fermentation space 4'$^v$ by pipe 72, which is U-shaped here. Vessel 71 is partially filled with a liquid 73, for example, with rain water. A U-shaped pipe 74 lies with one of its vertical arms 75 and with its horizontal section 76 in the dome 59. The upper end of the other vertical arm 75, on the other hand, projects through the bottom of the vessel and into the vessel, the two outlets of pipe 74 lying above the liquid level in vessel 71. Boreholes 78 are provided in that section of part 77, around which the liquid 73 circulates. Structure 1'ᵛ is embedded in the ground, its walls are insulated, even perhaps heated.

The equipment operates as follows. It is assumed that the equipment is filled to level 79 (FIG. 1) and that fermentation has commenced in fermentation space 3'ᵛ. The fresh material, brought in over feed pipe 66, filling shaft 9'ᵛ and the inlet opening 49, which is close to the bottom, liberates gas in the fermentation space 3'ᵛ, which collects in dome 59. The gas pressure, which develops here, forces the liquid level in fermentation space 3'ᵛ downwards and, at the same time, the liquid level outside of the fermentation space 3'ᵛ upwards (indicated by the dashed level lines 80 and 81), until the automatic valve mechanism 11'ᵛ responds. In the initial stage of considering the mode of action (level 79) the U-shaped part 74 is filled with liquid 73 from the vessel 71, because this liquid can flow into this part 74 through the boreholes 78, until the level is the same in the two communicating arms 75 and 77. Not only does the gas pressure, which is increasing in the fermentation space 3'ᵛ, lower the level in the fermentation space 3'ᵛ, as has already been mentioned, but it also simultaneously forces the liquid in the U-shaped pipe 74 back into the vessel 71 until the gas, which collects in the gas-collecting space 7'ᵛ, flows over this U-shaped pipe 74 into chamber 82, which is bounded by vessel 71, and from here over pipe 72 into the post-fermentation space 4'ᵛ. As a result, the pressure between spaces 3'ᵛ and 4'ᵛ is equalized so that subsequently the level in the fermentation space 3'ᵛ once again rises and the level in the post-fermentation space 4'ᵛ, on the other hand, once again falls until the pressure is equal in all the spaces (FIG. 1). The liquid, as its level rises in the post-fermentation space 4'ᵛ, passes through the bend of the siphon line 25'ᵛ, so that, as the level falls as a result of the pressure equalization described, fermenting sludge is pulled from chamber 60 through the siphon line 25'ᵛ and returned once again to the fermentation space 3'ᵛ. Because of the sludge falling from the siphon line 25'ᵛ and the grazing of the slanting ceiling 2'ᵛ by the alternately rising and falling level, the formation of a floating layer is successfully prevented. The material in the fermentation space 3'ᵛ is however also agitated to turbulence by the liquid flowing back from the post-fermentation space 4'ᵛ through the opening 54 at the bottom. This agitation also contributes to avoiding any formation of a floating layer. Excess liquid, which collects on ceiling 2'ᵛ, flows over the ridge edge of the ceiling 2'ᵛ into the vertical shaft 83 and is forced over the openings 67 near the bottom into the connecting rising vertical shafts 68 and 69, which form a siphon-like, hydraulic closure, from where it passes over the overflow edges 70 with adjustable height into the offtake 13'ᵛ. The warm, fermenting material, rising in shafts 68 and 69, transfers a portion of its heat over the internal bulkhead walls 62 and 63 to the charge in the filling shaft 9'ᵛ, so that this charge arrives in the fermentation space 3'ᵛ in a preheated state. In this manner, the heat contained by the fermented sludge which is to be removed, is returned in a practical fashion.

The described rise and fall of the sludge level takes place in a constant sequence, without external intervention. The frequency of this change depends on the nature of the fresh sludge, the size of the plant and on the existing temperatures. The biogas (methane gas), which collects in the post-fermentation space 4'ᵛ, is passed over pipe 12'ᵛ into the gas reservoir, expecially into a gasometer, which is not shown. Finally, FIG. 19 shows the principal design of the structural solutions shown in FIGS. 2–18. For the purpose of illustration, fermentation space 300 and post-fermentation space 400 are shown here as spatially separated structures. The upper portion of the fermentation space 300 changes into the tower- or shaft-like gas collecting space 700. The post-fermentation space 400, here spatially separate, is subdivided by wall panels 220 and 220' into individual chambers. Fermentation space 300 and post-fermentation space 400 are connected over the pipe section 200 in the nature of communicating parts. The discharge opening of this pipe section 200 in the bottom area of the post-fermentation space 400 is numbered 190. The offtake 130 leads from the post-fermentation space over a hydraulic closure 140, the inlet opening 150 of the offtake lying in the upper region of the post-fermentation space and moreover in or above the horizontal plane defined by the overflow edge 160 of the hydraulic closure. The siphon line 250 leads from the post-fermentation space 400 into the gas-collecting space 700 and moreover with a downwards directed curvature in order to form a hydraulic closure. Furthermore, FIG. 19 shows that, in the upper region of the filling shaft 90, arms are mounted which can swivel downwards from a horizontal position and which, in their horizontal position, project approximately to the center of the filling shaft. Valve 110, which is to be opened periodically, is mounted in pipe 100 which connects the gas-collecting space 700 with the upper region of the post-fermentation space 400, from which pipe 120 leads to a pressure equalizing container. The equalization level 310 is recorded in the individual spaces. It is reached, when the plant is in operation and a pressure equalization has taken place. The level, rising or falling as a result of the increase in gas pressure in the gas-collecting space 700, is indicated by the reference number 290.

If the plant is in operation and it is assumed that a gas exchange or a pressure equalization has just taken place over valve 110 and part 100, the level reached is given by the reference number 310. If gas is evolved in the fermentation space 300 after valve 110 is closed, this gas collects in the gas-collecting space 700 and forces the water level in the fermentation space 300 downwards. As a result, the level in the post-fermentation space 400 and also in the filling shaft 90 rises simultaneously until level 290 is reached. If valve 110 now opens up, the pressure difference between the gas-collecting space 700 and the post-fermentation space 400 is equalized with the result that the liquid level in the fermentation space 300 once again rises and the liquid level in the post-fermentation space 400 falls. In the first chamber of the post-fermentation space 400, which lies directly above the opening 190 of the pipe section 200, the level falls further than in the subsequent chambers, as a result of the height of the first partition 220'. During this pressure equalization, siphon line 250 also returns a portion of the liquid in the last chamber of the post-fermentation space 400 into the gas-collecting space 700, so that the liquid level in this last chamber also falls below the upper edge of the last partition 220. Valve 110 once again closes now and the process described commences once more.

Several arms 440 are tiltably hinged in filling shaft 90, preferably one above the other. As a rule, these arms han downwards. However, by the floating material, they are forced into a horizontal position which they cannot exceed. These arms project approximately to the center of the filling shaft and it is their task to prevent solids, which have reached the filling shaft, from constantly rising and falling as the level of the liquid alternately rises and falls. Any such solids in the filling shaft sink as the water level drops. If the pressure in the gas-collecting space 70 now increases, it forces the liquid once again up into the filling shaft. The liquid is able to rise. However, the solids, which have already sunk to the bottom, are prevented from rising, because, as they tend to rise, the tiltably mounted arms pivot into the horizontal position and restrain the solids. Consequently, the solids gradually sink deeper into the filling shaft and finally reach the fermentation space 300. Such restraining devices can of course also be mounted in the examples of the operation shown in FIGS. 2-18. They have not been shown there so as not to affect the clarity of the drawing.

Basically, it would also be possible to construct the equipment as shown in FIG. 19, that is, with spatially separated fermentation spaces. However, such a construction is space-consuming and, for this reason, a compact construction, as is shown in FIGS. 1-18 is generally preferred. Irrespective of this, the invention is intended to include also such equipment which has spatially separated fermentation and post-fermentation spaces.

I claim:

1. An apparatus for recovering methane gas from organic waste in thick sludge form comprising
    (a) a chamber sufficiently insulated to allow fermentation of organic waste to take place therein,
    (b) means within said chamber for dividing it into a fermentation space in its lower portion for holding fermenting organic waste, a gas collecting space above the fermenting space for trapping methane gas produced by fermenting waste so that gas trapped therein can cumulatively build up pressure on waste in the fermentation space and a post-collection space in the upper portion of the chamber,
    (c) communication means between the fermentation space and the post-collection space to allow flow of waste from the fermentation space into the post-collection space in response to gas pressure build up in the gas collection space and to allow flow of waste back into the fermentation space upon release of the pressure,
    (d) means for rapidly releasing the pressure of the gas in the gas-collection space to produce flow of waste from the post-collection chamber into the fermentation space of sufficient turbulence to effect break up of any gas impermeable layer which may form on the top of the waste,
    (e) means for activating the pressure release means and deactivating the pressure release means upon release of the pressure to allow a re-build up of pressure, and
    (f) means for introducing to and withdrawing waste from the chamber, wherein the post-fermentation space has an offtake with a hydraulic, siphon-like closure, and the gas-collecting space is connected with a valve means which periodically transfers the gas from the gas-collecting space into the post-fermentation space and at the same time discharges the sludge in portions through a siphon.

2. The apparatus of claim 1 wherein the activating and deactivating means are responsive to a given level of increased gas pressure in the gas collection space, a time interval or the volume of waste in the fermentation space.

3. The apparatus of claim 2, characterized by the fact that the false ceiling (2''', 2'ᵥ), which separates the fermentation space (3, 3''', 3'ᵥ) from the post-fermentation space (4, 4''', 4'ᵥ) is inclined (FIGS. 6, 7, 12).

4. The apparatus of claim 1, characterized by the fact that the post-fermentation space (4', 4'', 4'ᵥ) is arranged on the side of the gas-collecting space and that the gas-collecting space has ceilings (41, 48) of equal level and that a connecting opening (19, 54) to the fermentation space and the opening (15, 67) for the offtake are arranged at opposite ends of the post-fermentation space.

5. The apparatus of claim 1, characterized by the fact that, in the post-fermentation space (4') close to the bottom-side inlet opening (19), a wall panel (222) is provided which divides the post-fermentation space (4'), is connected with the bottom (2') of the post-fermentation space (4') but extends over only a portion of the internal height of the post-fermentation space (4').

6. The apparatus of claim 1 or 4, characterized by the fact that the post-fermentation space (4') is subdivided by vertical wall panels (22, 23) which are arranged in sequence in the direction of flow, these wall panels alternately being connected with the bottom (2') of the post-fermentation space (4') or positioned at a distance from the bottom, forming a gap (24).

7. The apparatus of claim 1, 2, 4 or 5, characterized by the fact that the discharge opening (35, 54) of the pipe, which connects the fermentation space and the post-fermentation space and which faces the fermentation space (3', 3''', 3'ᵥ) lies below the bottom of the post-fermentation space.

8. The apparatus of claim 1, characterized by the fact that the gas-collecting space is connected with the post-fermentation space by a siphon line (25, 25''', 25'ᵥ) and that the inlet opening of the siphon line is located in the bottom region of the post-fermentation space and the outlet opening in the upper region of the gas-collecting space.

9. The apparatus of claim 8, characterized by the fact that the siphon line (25) is passed first of all from its inlet opening near the bottom in a downwards curving arch so as to form a hydraulic closure (27) (FIG. 2).

10. The apparatus of claim 8, characterized by the fact that the siphon line (25''', 25'ᵥ) is mounted in a chamber (37, 60) which is connected with the post-fermentation space (4''', 4'ᵥ) and whose bottom (38, 55) lies below the bottom (2''', 2'ᵥ) of the post-fermentation space (4''', 4'ᵥ) (FIG. 7, FIG. 12).

11. The apparatus of claim 1, 2, 4, 5, 8, 9 or 10, characterized by the fact that the fermentation space (3') is constructed as an upright cylinder and the post-fermentation space (4') as a ring-shaped space lying above the cylinder and that the central part, hollowed out from the ring-shaped space, is connected with the fermentation space and functions as a gas-collecting space (7, 7'').

12. The apparatus of claim 11, characterized by the fact that the post-fermentation space (4''), constructed as a ring-shaped space (32) is subdivided by a central wall into two chambers, through which liquid flows in opposite directions (FIG. 5).

13. The apparatus of claim 1, characterized by the fact that at least one part of the offtake is heat-insulated and that moreover the supply line (9', 9'$^v$) in the fermentation space (3', 3'$^v$) passes through this part of the offtake (FIG. 2, FIG. 16.

14. The apparatus of claim 1 or 11, characterized by the fact that the inlet opening (15, 15') of the offtake (13, 13') from the post-fermentation space (4, 4') lies in the upper region of the post-fermentation space (4, 4') and, moveover, in or above the horizontal plane described by the overflow edge (16) of the hydraulic closure (14, 14') (FIG. 1, FIG. 2).

15. The apparatus of claim 1, characterized by the fact that the fermentation space (3'$^v$) has a second, inclined ceiling (2'$^v$) which covers the fermentation space and, for the purpose of forming a gas-collecting space (7'$^v$), lies lower than the ceiling (48) of structure (1'$^v$) and which goes over into a dome (59), and that the section of the post-fermentation space (4'$^v$), which lies next to the fermentation space (3'$^v$), is connected with the fermentation space by an opening (54) near the bottom.

16. The apparatus of claim 15, characterized by the fact the opening near the bottom extends like a slit over the width of the structural unit (1'$^v$) and that an essentially horizontal apron (55) extends from the upper edge (53) of the opening towards the fermentation space (4'$^v$) and that an essentially vertical partition (56) extends from the edge of the apron towards the ceiling (48) of the structural unit (1'$^v$), but ends before it reaches this ceiling, forming a slit.

17. The apparatus of claim 16, characterized by the fact that a siphon line (25'$^v$) which extends up to the apron (55) and discharges into the dome (59) of the gas-collecting space (7'$^v$), is mounted in a chamber (60), which is formed by the partition (56) and the wall (52) which forms the boundary between the fermentation space (3'$^v$) and the post-fermentation space (4'$^v$).

18. The apparatus of claim 16 or 17, characterized by the fact that the upper edge (58) of the partition (56) by a slight amount lies above the upper edge of the siphon line (25'$^v$).

19. The apparatus of claim 1 or 2, characterized by the fact that the partition (47), which forms the boundary of the fermentation space (3'$^v$) in the structural unit (1'$^v$) and which holds the inlet opening (49) for the waste, together with a front wall (46) of the structural unit 1'$^v$) forms a chamber (61) which is subdivided by at least four bulkhead partitions (62, 63, 64, 65) which are arranged symmetrically about the plane of the structural unit, the inner bulkhead partitions (62, 63) extending to the bottom (50) of the structural unit 1'$^v$) and forming the filling shaft (9'$^v$) and the two outer bulkhead partitions (64, 65) being detached from the bottom (50) of the structural unit (1'$^v$) so as to form openings (67) through which the liquid can flow (FIGS. 14, 16).

20. The apparatus of claim 19, characterized by the fact that the shafts (68, 69) which are bounded by the outer bulkhead walls (64, 65) discharge in their upper region into the offtake (13'$^v$) over overflow edges (70), whose height preferably is adjustable.

21. The apparatus of claim 19, characterized by the fact that the inner bulkhead walls (62, 63) are formed from profiled metal sheet.

22. The apparatus of claim 15, characterized by the fact that the valve mechanism (11'$^v$), provided in the dome (59) of the gas-collecting space (7'$^v$), consists of a pot-like chamber (82), which is partially filled with liquid (73) and which is connected through a pipe line (10'$^v$) with the post-fermentation space (4'$^v$), and of a U-shaped section of pipe (74), one of whose arms (75) lies in the upper region of the dome (59), the other (77) projecting into the pot-like chamber (82), while the discharge opening (84) lies above the liquid level and the section of the arm (77) around which the liquid washes, is provided with boreholes (78) (FIG. 18).

23. The apparatus of claim 22, characterized by the fact that the section (76) which connects the two vertical arms (75, 77) of the U-shaped section of pipe (74), runs essentially horizontally and preferably is longer than the distance between the arms (75, 77).

24. The apparatus of claim 1 or 2, characterized by the fact that, in the upper region of the filling shaft (90), arms (44) are provided, which can pivot from a horizontal position downwards and which, in their horizontal position, preferably project up to the center of the filling shaft (90) and that preferably several such arms are mounted along the height of the filling shaft (FIG. 19).

* * * * *